(12) United States Patent
Pavey

(10) Patent No.: US 7,439,355 B2
(45) Date of Patent: Oct. 21, 2008

(54) PROCESS FOR THE PRODUCTION OF OXABISPIDINES

(75) Inventor: John Pavey, Loughborough Leics (GB)

(73) Assignee: AstraZeneca AB, Sodertalje (SE)

( * ) Notice: Subject to any disclaimer, the term of this patent is extended or adjusted under 35 U.S.C. 154(b) by 281 days.

(21) Appl. No.: 11/089,325

(22) Filed: Mar. 25, 2005

(65) Prior Publication Data

US 2005/0171100 A1 Aug. 4, 2005

Related U.S. Application Data

(62) Division of application No. 10/381,900, filed on Mar. 31, 2003, now Pat. No. 6,936,712.

(30) Foreign Application Priority Data

| Oct. 2, 2000 | (PH) | 1-2000-02701 |
| Oct. 13, 2000 | (WO) | PCT/SE00/01994 |
| Oct. 1, 2001 | (WO) | PCT/SE01/02130 |

(51) Int. Cl.
*C07D 245/00* (2006.01)

(52) U.S. Cl. .................................... 540/470

(58) Field of Classification Search ................. 540/467, 540/470; 544/74
See application file for complete search history.

(56) References Cited

U.S. PATENT DOCUMENTS 6,559,143 B1 * 5/2003 Bjore et al. .............. 514/230.5

FOREIGN PATENT DOCUMENTS

| WO | WO 91/07405 | 5/1991 |
| WO | WO 99/31100 | 6/1999 |
| WO | WO 01/18992 A2 | 4/2001 |

OTHER PUBLICATIONS

Paudler, et al; "1,5-Bis(p-toluenesulfonyl)-3,7-Dihydroxyoctahydro-1,5-diazocine"; J. Org. Chem. 31, 277-280 (1966).

Dave et al; "Facile Preparation of 3,7-Diazabicyclo[3.3.0]octane . . . 1,5-Diazacyclooctane 3,7-Derivatives[1]"; J. Org. Chem.; 61(25), 8897-8903 (1996).

Chapman et al; "Difluoroamination of Heterocyclic Ketones: Control of Microbasicity"; J. Org. Chem. 63(5), 1566-1570 (1998).

Chapman et al; Nitrolysis of a Highly Deactivated Amide by Protonitronium. Synthesis and Structure of HNFX[1]; J. Org. Chem. 64(3), 960-965 (1999).

Paudler et al.; "3,7-Disubstituted Octahydro-1,5-diazocines. Their Conversion into . . . Ring-Contracted Products"; J. Org. Chem. 32, 2425-2430 (1967).

Chem. Ber. 96(11), 2827 (1963).

* cited by examiner

*Primary Examiner*—Kamal A Saeed
(74) *Attorney, Agent, or Firm*—Nixon & Vanderhye

(57) ABSTRACT

There is provided a process for the preparation of a compound of formula I, (I), or a pharmaceutically acceptable derivative thereof, wherein A, B, G, $R^1$, $R^2$, $R^3$, $R^4$ and $R^{41}$ to $R^{46}$ have meanings given in the description, which process comprises the dehydrative cyclisaton of a compound of formula II. (II).

2 Claims, No Drawings

PROCESS FOR THE PRODUCTION OF OXABISPIDINES

This Application is a divisional of U.S. application Ser. No. 10/381,900, filed Mar. 31, 2003, now U.S. Pat. No. 6,936,712, the entire contents of which is hereby incorporated by reference in this Application.

FIELD OF THE INVENTION

This invention relates to a novel process for the preparation of compounds comprising the oxabispidine ring system.

PRIOR ART

The number of documented compounds including the 9-oxa-3,7-diazabicyclo-[3.3.1]nonane (oxabispidine) structure is very few. As a result, there are very few known processes that are specifically adapted for the preparation of oxabispidine compounds.

Certain oxabispidine compounds are disclosed in *Chem. Ber.* 96(11), 2827 (1963) as intermediates in the synthesis of 1,3-diaza-6-oxa-adamantanes.

Hemiacetals (and related compounds) having the oxabispidine ring structure are disclosed in *J. Org. Chem.* 31, 277 (1966), ibid. 61(25), 8897 (1996), ibid. 63(5), 1566 (1998) and ibid. 64(3), 960 (1999) as unexpected products from the oxidation of 1,5-diazacyclooctane-1,3-diols or the reduction of 1,5-diazacyclooctane-1,3-diones.

1,3-Dimethyl-3,7-ditosyl-9-oxa-3,7-diazabicyclo[3.3.1]nonane is disclosed in *J. Org. Chem.* 32, 2425 (1967) as a product from the attempted acetylation of trans-1,3-dimethyl-1,5-ditosyl-1,5-diazacyclooctane-1,3-diol.

None of the above-mentioned documents disclose or suggest the synthesis of oxabispidines by way of dehydrative cyclisation of a 3,7-dihydroxy-1,5-diazacyclooctane.

We have now found, surprisingly, that such compounds may be made efficiently by way of such a cyclisation process, which process is capable of being scaled up.

DESCRIPTION OF THE INVENTION

According to a first aspect of the invention there is provided a process for the preparation of a compound of formula I,

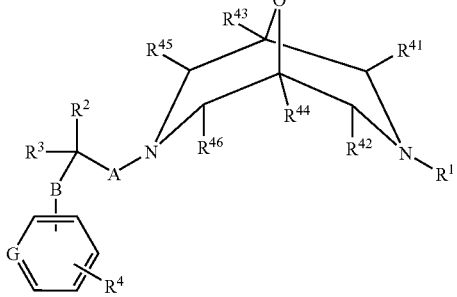

I wherein
$R^1$ represents $C_{1-12}$ alkyl (which allyl group is optionally substituted and/or terminated by one or more groups selected from halo, cyano, nitro, aryl, $Het^1$, —C(O)$R^{5a}$, —O$R^{5b}$, —N($R^6$)$R^{5c}$, —C(O)X$R^7$, —C(O)N($R^8$)$R^{5d}$, and —S(O)$_2R^9$), or $R^1$ represents —C(O)X$R^7$, —C(O)N($R^8$)$R^{5d}$ or —S(O)$_2R^9$;

$R^{5a}$ to $R^{5d}$ independently represent, at each occurrence, H, $C_{1-6}$ alkyl (which latter group is optionally substituted and/or terminated by one or more substituents selected from —OH, halo, cyano, nitro, aryl and $Het^2$), aryl or $Het^3$, or $R^{5d}$, together with $R^8$, represents $C_{3-6}$ alkylene (which alkylene group is optionally interrupted by an O atom and/or is optionally substituted by one or more $C_{1-3}$ alkyl groups);

$R^6$ represents H, $C_{1-6}$ alkyl (optionally substituted and/or terminated by one or more substituents selected from —OH, halo, cyano, nitro and aryl), aryl, —C(O)$R^{10a}$, —C(O)O$R^{10b}$ or —C(O)N(H)$R^{10c}$;

$R^{10a}$, $R^{10b}$ and $R^{10c}$ independently represent $C_{1-6}$- alkyl (optionally substituted and/or terminated by one or more substituents selected from —OH, halo, cyano, nitro and aryl), aryl, or $R^{10a}$ a represents H;

$R^7$ represents $C_{1-12}$ alkyl (optionally substituted and/or terminated by one or more substituents selected from —OH, halo, cyano, nitro, aryl, $C_{1-6}$ alkoxy and $Het^4$);

$R^8$ represents H, $C_{1-12}$ alkyl, $C_{1-6}$ alkoxy (which latter two groups are optionally substituted and/or terminated by one or more substituents selected from —OH, halo, cyano, nitro, $C_{1-4}$ alkyl and $C_{1-4}$ alkoxy), -D-aryl, -D-aryloxy, -D-$Het^5$, -D-N(H)C(O)$R^{11a}$, -D-S(O)$_2$ $R^{12a}$, -D-C(O)$R^{11b}$, -D-C(O)O$R^{12b}$, -D-C(O)N($R^{11c}$) $R^{11d}$, or $R^8$, together with $R^{5d}$, represents $C_{3-6}$ alkylene (which alkylene group is optionally interrupted by an O atom and/or is optionally substituted by one or more $C_{1-3}$ alkyl groups);

$R^{11a}$ to $R^{11d}$ independently represent H, $C_{1-6}$ alkyl (optionally substituted and/or terminated by one or more substituents selected from —OH, halo, cyano, nitro and aryl), aryl, or $R^{11c}$ and $R^{11d}$ together represent $C_{3-6}$ alkylene;

$R^9$, $R^{12a}$ and $R^{12b}$ independently represent $C_{1-6}$ alkyl (optionally substituted and/or terminated by one or more substituents selected from —OH, halo, cyano, nitro and aryl) or aryl;

D represents a direct bond or $C_{1-6}$ alkylene;
X represents O or S;
$R^2$ represents H, halo, $C_{1-6}$ alkyl, —O$R^{13}$, -E-N($R^{14}$)$R^{15}$ or, together with $R^3$, represents =O;
$R^3$ represents H, $C_{1-6}$ alkyl or, together with $R^2$, represents =O;
$R^{13}$ represents H, $C_{1-6}$ alkyl, -E-aryl, -E-$Het^6$, —C(O)$R^{16a}$, —C(O)O$R^{16b}$ or —C(O)N($R^{17a}$)$R^{17b}$;
$R^{14}$ represents H, $C_{1-6}$ alkyl, -E-aryl, -E-$Het^6$, —C(O)$R^{16a}$, —C(O)O$R^{16b}$, —S(O)$_2R^{16c}$, —[C(O)]$_p$N($R^{17a}$)$R^{17b}$ or —C(NH)NH$_2$;
$R^{15}$ represents H, $C_{1-6}$ all, -E-aryl or —C(O)$R^{16d}$;
$R^{16a}$ to $R^{16d}$ independently represent, at each occurrence when used herein, $C_{1-6}$ alkyl (optionally substituted and/or terminated by one or more substituents selected from halo, aryl and $Het^7$), aryl, $Het^8$, or $R^{16a}$ and $R^{16d}$ independently represent H;
$R^{17a}$ and $R^{17b}$ independently represent, at each occurrence when used herein, H or $C_{1-6}$ alkyl (optionally substituted and/or terminated by one or more substituents selected from halo, aryl and $Het^9$), aryl, $Het^{10}$, or together represent $C_{3-6}$ alkylene, optionally interrupted by an O atom;
E represents, at each occurrence when used herein, a direct bond or $C_{1-4}$ alkylene;
p represents 1 or 2;
$Het^1$ to $Het^{10}$ independently represent five- to twelve-membered heterocyclic groups containing one or more heteroatoms selected from oxygen, nitrogen and/or sulfur, which groups are optionally substituted by one or more substituents selected from —OH, oxo, halo, cyano, nitro, $C_{1-6}$ alkyl, $C_{1-6}$ alkoxy, aryl, aryloxy, —N($R^{18a}$)$R^{18b}$, —C(O)$R^{18c}$, —C(O)O$R^{18d}$, —C(O)N ($R^{18e}$)$R^{18f}$, —N($R^{18g}$)C(O)$R^{18h}$ and —N($R^{18i}$)S(O)$_2$ $R^{18j}$;

$R^{18a}$ to $R^{18j}$ independently represent $C_{1-6}$ alkyl, aryl or $R^{18a}$ to $R^{18j}$ independently represent H;

A represents a direct bond, -J-, -J-N($R^{19}$)— or -J-O— (in which latter two groups, N($R^{19}$)— or O— is attached to the carbon atom bearing $R^2$ and $R^3$);

B represents -Z-, -Z-N($R^{20}$)—, —N($R^2$-Z-, -Z-S(O)$_n$—, -Z-O— (in which latter two groups, Z is attached to the carbon atom bearing $R^2$ and $R^3$), —N($R^{20}$)C(O)O-Z-, (in which latter group, —N($R^{20}$) is attached to the carbon atom bearing $R^2$ and $R^3$) or —C(O)N($R^{20}$)— (in which latter group, —C(O) is attached to the carbon atom bearing $R^2$ and $R^3$);

J represents $C_{1-6}$ alkylene optionally substituted by one or more substituents selected from —OH, halo and amino;

Z represents a direct bond or $C_{1-4}$ alkylene;

n represents 0, 1 or 2;

$R^{19}$ and $R^{20}$ independently represent H or $C_{1-6}$ alkyl;

G represents CH or N;

$R^4$ represents one or more optional substituents selected from —OH, cyano, halo, nitro, $C_{1-6}$ alkyl (optionally terminated by —N(H)C(O)O$R^{21a}$), $C_{1-6}$ alkoxy, —N($R^{22a}$)$R^{22b}$, —C(O)$R^{22c}$, C(O)O$R^{22d}$, C(O)N($R^{22e}$)$R^{22f}$, —N($R^{22g}$)C(O)$R^{22h}$, —N($R^{22i}$)C(O)N($R^{22j}$)$R^{22k}$, —N($R^{22m}$)S(O)$_2$$R^{21b}$, —S(O)$_2$$R^{21c}$, and/or —OS(O)$_2$ $R^{21d}$;

$R^{21a}$ to $R^{2ad}$ independently represent $C_{1-6}$ allyl;

$R^{22a}$ and $R^{22b}$ independently represent H, $C_{1-6}$ alkyl or together represent $C_{3-6}$ alkylene, resulting in a four- to seven-membered nitrogen-containing ring;

$R^{22a}$ to $R^{22m}$ independently represent H or $C_{1-6}$ alkyl; and $R^{41}$ to $R^{46}$ independently represent H or $C_{1-3}$ alkyl;

wherein each aryl and aryloxy group, unless otherwise specified, is optionally substituted;

provided that (a) when A represents -J-N($R^{19}$ or -J-O—, then:
   (i) J does not represent $C_1$ alkylene; and
   (ii) B does-not represent —N($^{20}$)—, —N($R^{20}$)-Z- (in which latter group N($R^{20}$) is attached to the carbon atom bearing $R^2$ and $R^3$), —S(O)$_n$, —O— or —N($^{20}$) C(O)O-Z- when $R^2$ and $R^3$ do not together represent =O; and (b) when $R^2$ represents —O$R^{13}$ or —N$R^{14}$)($R^{15}$), then:
   (i) A does not represent -J-N($R^{19}$)— or -J-O—; and
   (ii) B does not represent —N($R^{20}$)—, —N($R^2$)-Z- (in which latter group N($R^{20}$) is attached to the carbon atom bearing $R^2$ and $R^3$), —S(O)$_n$—, —O— or —N($R^{20}$)C(O)O-Z-;

or a pharmaceutically acceptable derivative thereof;

which process comprises the dehydrative cyclisation of a compound of formula II,

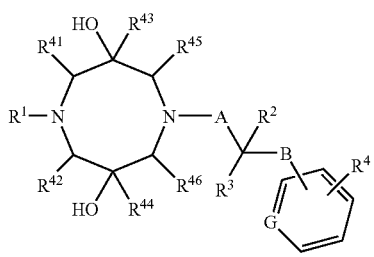

wherein A, B, G, $R^1$, $R^2$, $R^3$, $R^4$ and $R^{41}$ to $R^{46}$ are as hereinbefore defined, which process is referred to hereinafter as "the process of the invention".

Unless otherwise specified, allyl groups and alkoxy groups as defined herein may be straight-chain or, when there is a sufficient number (i.e. a minimum of three) of carbon atoms be branched-chain, and/or cyclic. Further, when there is a sufficient number (i.e. a minium of four) of carbon atoms, such alkyl and alkoxy groups may also be part cyclic/acyclic. Such alkyl and alkoxy groups may also be saturated or, when there is a sufficient number (i.e. a minimum of two) of carbon atoms, be unsaturated and/or interrupted by one or more oxygen and/or sulfur atoms. Unless otherwise specified, alkyl and alkoxy groups may also be substituted by one or more halo, and especially fluoro, atoms.

Unless otherwise specified, alkylene groups as defined herein may be straight-chain or, when there is a sufficient number (i.e. a minimum of two) of carbon atoms, be branched-chain. Such alkylene chains may also be saturated or, when there is a sufficient number (i.e. a minimum of two) of carbon atoms, be unsaturated and/or interrupted by one or more oxygen and/or sulfur atoms. Unless otherwise specified, alkylene groups may also be substituted by one or more halo atoms.

The term "aryl", when used herein, includes $C_{6-10}$ aryl groups such as phenyl, naphthyl and the like. The term "aryloxy", when used herein includes $C_{6-10}$ aryloxy groups such as phenoxy, naphthoxy and the like. For the avoidance of doubt, aryloxy groups referred to herein are attached to the rest of the molecule via the O-atom of the oxy-group. Unless otherwise specified, aryl and aryloxy groups may be substituted by one or more substituents including —OH, halo, cyano, nitro, $C_{1-6}$ alkyl, $C_{1-6}$ alkoxy, N($R^{22a}$)$R^{22b}$, —C(O) $R^{22c}$, —C(O)O$R^{22d}$, —C(O)N($R^{22e}$)$R^{22f}$, —N($R^{22g}$)C(O) $R^{22h}$b, —S(O)$_2$$R^{21b}$, and/or —OS(O)$_2$$R^{21c}$, and/or —OS (O)$_2$ $R^{21d}$ (wherein $R^{21b}$ to $R^{21d}$ and $R^{22a}$ to $R^{22m}$ are as hereinbefore defined). When substituted, aryl and aryloxy groups are preferably substituted by between one and three substituents.

The term "halo", when used herein, includes fluoro, chloro, bromo and iodo.

Het (Het$^1$, Het$^2$, Het$^3$, Het$^4$, Het$^5$, Het$^6$, Het$^7$, Het$^8$, Het$^9$ and Het$^{10}$) groups that may be mentioned include those containing 1 to 4 heteroatoms (selected from the group oxygen, nitrogen and/or sulfur) and in which the total number of atoms in the ring system are between five and twelve. Het (Het$^1$, Het$^2$, Het$^3$, Het$^4$, Het$^5$, Het$^6$, Het$^7$, Het$^8$, Het$^9$ and Het$^{10}$) groups may be fully saturated, wholly aromatic, partly aromatic and/or bicyclic in character. Heterocyclic groups that may be mentioned include benzodioxanyl, benzodioxepanyl, benzodioxolyl, benzofuranyl; benzimidazolyl, benzomorpholinyl, benzoxazinonyl, benzothiophenyl, chromanyl, cinnolinyl, dioxanyl, furanyl, imidazolyl, imidazo[1,2-a]pyfidinyl, indolyl, isoquinolinyl, isoxazolyl, morpholinyl, oxazolyl, phthalazinyl, piperazinyl, piperidinyl, purinyl, pyranyl, pyrazinyl, pyrazolyl, pyridinyl, pyrimindinyl, pyrrolidinonyl, pyrrolidinyl, pyrrolinyl, pyrrolyl, quinazolinyl, quinolinyl, tetrahydropyranyl, tetrahydrofuranyl, thiazolyl, thienyl, thiochromanyl, triazolyl and the like. Values of Het$^1$ that may be mentioned include pyridinyl, benzodioxanyl, imidazolyl, imidazo[1,2-a]pyridinyl, piperazinyl, pyrazolyl, pyrrolyl, pyrrolidinyl, tetrahydropyranyl and thiazolyl. Values of Het$^3$ that may be mentioned include benzodioxanyl and benzomorpholinyl. Values of Het$^4$ that may be mentioned include piperazinyl. Substituents on Het (Het$^1$, Het$^2$, Het$^3$, Het$^4$, Het$^5$, Het$^6$, Het$^7$, Het$^8$, Het$^9$ and Het$^{10}$) groups may, where appropriate, be located on any atom in the ring system including a heteroatom. The point of attachment of Het (Het$^1$, Het$^2$, Het$^3$, Het$^4$, Het$^5$, Het$^6$, Het$^7$, Het$^8$, Het$^9$ and Het$^{10}$) groups may be via any atom in the ring system including (where appropriate) a heteroatom, or an atom on any fused carbocyclic ring that may be present as part of the ring system.

Het ($Het^1$, $Het^2$, $Het^3$, $Het^4$, $Het^5$, $Het^6$, $Het^7$, $Het^8$, $Het^9$ and $Het^{10}$) groups may also be in the N— or S-oxidised form.

Pharmaceutically acceptable derivatives include salts and solvates. Salts which may be mentioned include acid addition salts. Specific salts that may be mentioned include alkanesulfonate salts, such as methanesulfonate, arylsulfonate salts, such as toluenesulfonate and, especially, benzenesulfonate salts. Solvates that may be mentioned include hydrates, such as monohydrates.

Pharmaceutically acceptable derivatives also include, at the oxabispidine or (when G represents N) pyridyl nitrogens, $C_{1-4}$ alkyl quaternary ammonium salts and N-oxides, provided that when a N-oxide is present:

(a) no Het ($Het^1$, $Het^2$, $Het^3$, $Het^4$, $Het^5$, $Het^6$, $Het^7$, $Het^8$, $Het^9$ and $Het^{10}$) group contains an unoxidised S-atom; and/or (b) n does not represent 0 when B represents -Z-S(O)$_n$—.

It is preferred that the compound of formula I is not 3,7-dibenzoyl-9-oxa-3,7-diazabicyclo[3.3.1]nonane.

It is preferred that, in the compounds of formulae I and II, the substituent $R^{42}$ has the same identity as $R^{41}$, $R^{44}$ has the same identity as $R^{43}$ and $R^{46}$ has the same identity as $R^{45}$. It is preferred that $R^{41}$ to $R^{46}$ independently represent H.

Compounds of formulae I and II that may be mentioned include those in which, when $R^2$ and $R^3$ together represent =O, then A and B do not simultaneously represent direct bonds.

Preferred compounds of formulae I and II include those in which the group $R^1$ and the group

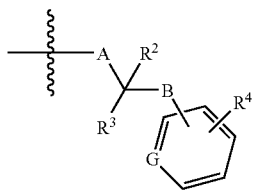

are different, and as such include those compounds of formulae I and II in which $R^1$ represents —C(O)X$R^7$, —C(O)N($R^8$)$R^{5d}$ d or —S(O)$_2R^9$ (wherein X, $R^{5d}$, $R^7$, $R^8$ and $R^9$ are as hereinbefore defined).

Particularly preferred compounds of formulae I and E include those in which $R^1$ represents —S(O)$_2R^9$, wherein $R^9$ represents optionally substituted aryl (such as optionally substituted phenyl, including 2- or 4fluorophenyl, 2- or 4-chlorophenyl, 4-bromophenyl, 4methylphenyl, 4methoxyphenyl, 2-nitrophenyl, 2, dinitrophenyl, 2,4,6-trimethylphenyl and, especially, unsubstituted phenyl or 4nitrophenyl);

$R^{41}$ to $R^{46}$ all represent H;

G represents CH;

A represents a direct bond;

B represents a direct bond;

$R^2$ represents H or $C_{1-6}$ alkyl;

$R^3$ represents H or $C_{1-6}$ alkyl;

$R^4$ is absent (i.e. the ring is unsubstituted) or represents one to three halo, methyl, methoxy or nitro groups, especially 2- or 4-fluoro, 2- or 4-chloro, 4-bromo, 4-methyl, 2,4,6-trimethyl, 4-methoxy, or 2- or 4-nitro.

Preferred compounds of formula I may also include those in which:

$R^1$ represents straight- or branched-chain $C_{1-4}$ alkyl (e.g. $C_{1-3}$ allyl) terminated by —C(O)$R^{5a}$ or —N(H)C(O)O$R^{10b}$;

$R^{5a}$ and $R^{10b}$ independently represent straight- or branched-chain $C_{2-6}$ alkyl (e.g. $C_{3-5}$ alkyl, such butyl (e.g. t-butyl));

$R^2$ represents H or OH;

A represents $C_{1-2}$ alkylene;

B represents -Z-, -Z-N(H)— or -Z-O— (in which latter two groups, Z is attached to the carbon atom bearing $R^2$ and $R^3$, and represents $C_{1-2}$ alkylene);

$R^4$ is a single cyano group in the para-position relative to B.

The process of the -invention may be carried out, for example in the presence of a suitable dehydrating agent (such as: a strong acid (e.g. sulfuric acid (e.g. concentrated sulfuric acid), methanesulfonic acid (e.g. anhydrous methanesulfonic acid) and the like); an acid anhydride such as acetic anhydride or trifluoromethane-sulfonic anhydride; $P_2O_5$ in methanesulfonic acid; a phosphorous-based halogenating agent such as P(O)Cl$_3$, PCl$_3$ or PCl$_5$; or thionyl chloride).

The process of the invention may also be carried out in the presence of a suitable organic solvent system, which solvent system should not significantly react chemically with, or significantly give rise to stereochemical changes in, the reactant or product once formed, or significantly give rise to other side reactions. Preferred solvent systems include aromatic solvent (e.g. toluene, xylene, chlorobenzene or dichlorobenzene), or dichloroethane, optionally in the presence of further solvents such as ethanol and/or ethyl acetate.

When the dehydrating agent is methanesulfonic acid, preferred solvent systems include toluene. When the dehydrating agent is sulfuric acid, preferred solvent systems include chlorobenzene or no solvent.

The process of the invention may be carried out at elevated temperature (e.g. up to the reflux temperature of the relevant solvent system, or higher if a pressurised system is employed). Clearly, appropriate reaction times and reaction temperatures depend upon the solvent system that is employed, as well as the reactants that are used and the compound that is to be formed, but these may be determined routinely by the skilled person.

Compounds of formula II may advantageously be prepared by reaction of a compound of formula III,

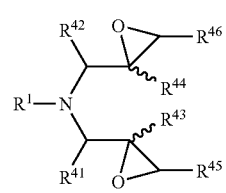

III wherein the wavy bonds indicate optional R—, S— or mixed R— and S— stereochemistry at the asymmetric carbon atoms, and $R^1$ and $R^{41}$ to $R^{46}$ are as hereinbefore defined, with a compound of formula IV,

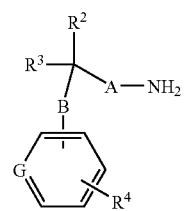

IV wherein $R^2$, $R^3$, $R^4$, A, B and G are as hereinbefore defined. This reaction may be carried out at between room temperature and the reflux temperature of any solvent that is employed (preferably at or around reflux temperature). Suitable solvent systems that may be employed include organic solvent systems, which systems should not significantly react chemically with, or significantly give rise to stereochemical changes in, the reactants or product once formed, or significantly give rise to other side reactions. Preferred solvent systems include hydroxylic compounds such as ethanol, methanol, propan-2-ol, or mixtures thereof (such as industrial methylated spirit (IMS)), optionally in the presence of an appropriate co-solvent (e.g. an ester, such as ethyl acetate, an aromatic solvent, such as toluene or chlorobenzene, or water). Preferred solvents for this reaction include primary alcohols such as methanol, propanol and, especially, ethanol, and preferred co-solvents include toluene and chlorobenzene.

The reaction of a compound of formula II with a compound of formula IV to form a compound of formula II, and the subsequent cyclisation to form a compound of formula I by way of the process of the invention, may also be carried by way of a direct "one-pot" procedure, for example as described hereinafter.

The formation of compounds of formula II may also be performed using compounds of formula In having enantiomeric (or diastereomeric) enrichment at the chiral centres identified hereinbefore. The use of such enantiomerically- (or diastereomerically-) enriched compounds of formula HI in the formation of compounds of formula II may have the advantage that a greater proportion of the product diol is obtained in a form (e.g. the trans-form) which facilitates the subsequent cyclisation, leading to a higher yield of compounds of formula I.

The formation of compounds of formula It is preferably carried out using compounds of formula III in which $R^1$ represents —C(O)$XR^7$, —C(O)N($R^8$)$R^{5d}$ or —S(O)$_2R^9$ and X, $R^{5d}$, $R^7$, $R^8$ and $R^9$ are as hereinbefore defined. The formation of compounds of formula II is more preferably carried out using compounds of formula in in which $R^1$ represents —S(O)$^2R^9$ (e.g. wherein $R^9$ represents optionally substituted phenyl, such as 2- or 4-fluorophenyl, 2- or 4-chlorophenyl, 4-bromophenyl, 4-methylphenyl, 4methoxyphenyl, 2-nitrophenyl, 2,4-dinitrophenyl, 2,4,6-trimethylphenyl and, especially, unsubstituted phenyl or 4-nitrophenyl).

Preferred compounds of formula IV include those in which:

G represents CH;
A represents a direct bond;
B represents a direct bond;
$R^2$ represents H or $C_{1-6}$ alkyl;
$R^3$ represents H or $C_{1-6}$ alkyl;
$R^4$ is absent or represents one to three halo, methyl, methoxy or nitro groups, especially 2- or 4-fluoro, 2- or 4-chloro, 4-bromo, 4-methyl, 2,4,6-trimethyl, 4-methoxy, or 2- or 4-nitro.

Especially preferred compounds of formula IV include those in which $R^4$ is absent (i.e. the ring is unsubstituted).

We have found, surprisingly, that when compounds of formula I are formed using the process of the invention, the employment of derivatives of formula III in which $R^1$ represents —C(O)$XR^7$, —C(O)N($R^8$)$R^{5d}$ or, especially, —S(O)$_2$$R^9$ (e.g. wherein $R^1$ represents optionally-substituted benzenesulfonyl, as described above), and benzylamine-type derivatives of formula IV (such as those described above) to produce compounds of formula II, may have the advantage that, in the resultant compound of formula I, the presence of the $R^1$ (e.g. —S(O)$_2R^9$) group and/or the benzylamine-type group allows for direct and facile replacement of that/those group(s) with other $R^1$ groups, and/or

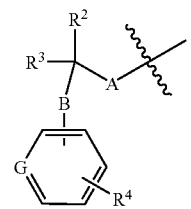

fragments, as appropriate, for example by employing reactions that are akin to "deprotection" reactions (see below), and subsequently performing coupling reactions.

We have found that, if benzenesulfonyl derivatives of formula III, and benzylamine-type derivatives of formula IV are employed, subsequent replacement steps may be made more straightforward (e.g. enabling the use of milder reaction conditions).

In this respect, certain compounds of formula I may be employed as intermediates, useful in the manufacture of other compounds of formula I. Such compounds include, but are not limited to, preferred compounds of formula I mentioned hereinbefore and, particularly, compounds of formula I in which:

$R^2$ and $R^3$ both represent H;
$R^4$ is absent; and/or
$R^9$ represents unsubstituted phenyl or 4-nitrophenyl.
Further, compounds of formula I in which:
$R^{41}$ to $R^{46}$ all represent H;
$R^1$ represents straight- or branched-chain $C_{1-4}$ alkyl (e.g. $C_{k_3}$ alkyl, such as methyl or ethyl) terminated by C(O)$R^{5a}$ or —N(H)C(O)OR$^{10b}$;
$R^{5a}$ and $R^{10b}$ independently represent straight- or branched-chain $C_{2-6}$ all (e.g. $C_{3-5}$ alkyl, such butyl (e.g. t-butyl));
$R^2$ represents H or OH;
$R^3$ represents H;
A represents $C_1$ alkylene or linear $C_2$ alkylene;
B represents -Z-, -Z-N(H)— or -Z-O— (in which latter two groups, Z is attached to the carbon atom bearing $R^2$ and $R^3$, and represents $C_1$ alkylene or linear $C_2$ alkylene);
G represents CH; and
R is a single cyano group in the para-position relative to B.
may be prepared by a process which comprises the steps of:
  (i) removal of the —SO$_2R^9$ group from a compound of formula I (formed by way of the process of the invention) in which $R^1$ represents —S(O)$_2R^9$, wherein $R^9$ represents optionally substituted phenyl as hereinbefore defined, $R^{41}$ to $R^{46}$ all represent H, G represents CH, A and B both represent direct bonds, $R^2$ and $R^3$ independently represent H or $C_{1-6}$ alkyl and $R^4$ is absent or represents one to three halo, methyl, methoxy or nitro groups (e.g. 2- or 4-fluoro, 2- or 4-chloro, 4-bromo, 4-methyl, 2,4,6-trimethyl, 4-methoxy, or 2- or 4-nitro), to provide a compound of formula V,

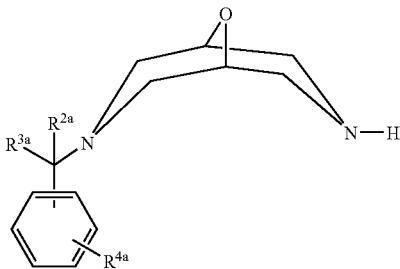

V (iii) removal of the

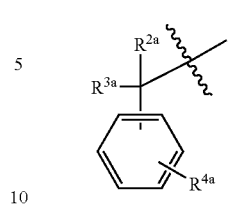

fragment from the resultant compound of formula I to provide a compound of formula VII,

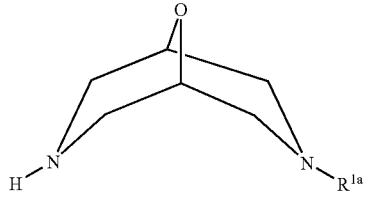

VII wherein $R^{1a}$ is as hereinbefore defined, for example under appropriate deprotection conditions, such as hydrogenation in the presence of a supported palladium catalyst (e.g. Pd/C), for example at room temperature in the presence of a suitable solvent (e.g. a lower alkyl alcohol, such as ethanol)); and (iv) either (a) reaction of the resultant compound of formula VII with a compound of formula VIII,

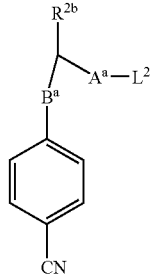

VIII in which $R^{2a}$ and $R^{3a}$ represents H or $C_{1-6}$ alkyl and $R^{4a}$ represents an optional substituent, selected from one to three halo, methyl, methoxy or nitro groups (e.g. 2- or 4-fluoro, 2- or 4-chloro, 4-bromo, 4-methyl, 2,4,6-trimethyl, 4-methoxy, or 2- or 4-nitro), for example using standard deprotection conditions (e.g. in the presence of a standard deprotecting agent (such a hydrohalic acid (e.g. HBr, especially concentrated aqueous HBr), or a nucleophile such as mercaptoacetic acid di-lithium salt, potassium hydroxide, potassium tert-butoxide, or sodium or potassium thiophenolate, or a reducing agent such as $LiAlH_4$), at or above room temperature (e.g. at reflux) with or without the presence of a solvent);

(ii) reaction of the resultant compound of formula V with a compound of formula VI, $$R^{1a}\text{-}L^1 \qquad \qquad VI$$

wherein $R^{1a}$ represents straight- or branched-chain $C_{1-4}$ alkyl (e.g. $C_{1-3}$ alkyl, such as methyl or ethyl) terminated by C(O)$R^{5a}$ or —N(H)C(O)O$R^{10b}$, in which $R^{5a}$ and $R^{10b}$ independently represent straight- or branched-chain $C_{2-6}$ alkyl (e.g. $C_{3-5}$ alkyl, such butyl (e.g. t-butyl)), and $L^1$ represents a leaving group such as halo, alkanesulfonate, perfluoroalkanesulfonate, arenesulfonate, —OC(O)X$R^7$, imidazole or $R^{23}$O— (wherein $R^{23}$ represents, for example, $C_{1-10}$ allyl or aryl, which groups are optionally substituted by one or more halo or nitro groups) and X and $R^7$ are as hereinbefore defined, to form a compound of formula I in which $R^1$ represents straight- or branched-chain $C_{1-4}$ alkyl (e.g. $C_{1-3}$ alkyl, such as methyl or ethyl) terminated by C(O)$R^{5a}$ or —N(H)C(O)O$R^{10b}$, $R^{5a}$ and $R^{10b}$ independently represent straight- or branched-chain $C_{2-6}$ alkyl (e.g. $C_{3-5}$ alkyl, such butyl (e.g. t-butyl)), $R^{41}$ to $R^{46}$ all represent H, G represents CH, A and B both represent a direct bond, $R^2$ and $R^3$ independently represent H or $C_{1-6}$ alkyl and $R^4$ is absent or represents one to three halo, methyl, methoxy or nitro groups (e.g. 2- or 4-fluoro, 2- or 4-chloro, 4-bromo, 4-methyl, 2,4,6-trimethyl, 4-methoxy, or 2- or 4-nitro), for example at between room and reflux temperature in the presence of a suitable base (e.g. triethylamine, potassium carbonate or a bicarbonate, such as sodium bicarbonate) and an appropriate solvent (e.g. dichloromethane, chloroform, acetonitrile, NIV-dimethylformamide, TBF, toluene, water, a lower alkyl alcohol (e.g. ethanol) or mixtures thereof), more preferably in the presence of a suitable solvent (e.g. water, a lower alkyl alcohol, acetonitrile, or mixtures thereof) and an appropriate base (e.g. sodium bicarbonate or potassium carbonate);

wherein $L^2$ represents a suitable leaving group, such as halo, arenesulfonate, perfluoroalkanesulfonate or alkanesulfonate (e.g. p-toluenesulfonate, 2- or 4-nitrobenzenesulfonate, methanesulfonate, benzenesulfonate or trifluoromethanesulfonate), $R^{2b}$ represents H or OH, $A^a$ represents $C_1$ alkylene or linear $C_2$ alkylene and $B^a$ represents -Z-, -Z-N(H)— or -Z-O— (in which latter two groups, Z is attached to the carbon atom bearing $R^{2b}$, and represents $C_1$ alkylene or linear $C_2$ alkylene), for example at elevated temperature (e.g. between 35° C. and reflux temperature) in the presence of a suitable base (e.g. triethylamine or potassium carbonate) and an appropriate organic solvent (e.g. acetonitrile, dichloromethane, chloroform, dimethylsulfoxide, N,N-dimethylformamide, a lower alkyl alcohol (e.g. ethanol), isopropyl acetate or mixtures thereof, more preferably at between room and reflux temperature, in the presence of a suitable base (e.g. potassium carbonate) and an appropriate organic solvent (e.g. a lower alkyl alcohol, such as ethanol); or (b), for compounds of formula I in which A represents $CH_2$ and $R^2$ represents —OH, reaction of a compound of formula VII, as hereinbefore defined, with a compound of formula IX,

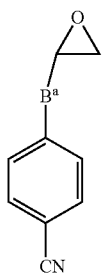

IX wherein $B^a$ is as hereinbefore defined, for example at elevated temperature (e.g. 60° C. to reflux) in the presence of a suitable solvent (e.g. a lower alkyl alcohol (e.g. IPA)), acetonitrile, or a mixture of a lower alkyl alcohol and water).

The skilled person will appreciate that, if desired, the above steps may be performed in a different order to those stated above, to provide the relevant compounds of formula I. For example, steps (iii) and (iv) may be carried out prior to steps (i) and (ii). Alternatively, steps (i) and (iii) (in either order) may be completed before steps (ii) and (iv) (in either order) are carried out.

Further, it will be appreciated by the skilled person that it may be desirable to protect the free nitrogen following the completion of step (i) with an alternative protecting group (e.g. a tert-butyloxycarbonyl group) prior to the carrying out of step (ii) which, as stated above, may be carried out prior to or after steps (iii) and (iv) (following deprotection, as appropriate).

It is preferred that steps (i) to (iv) are employed to prepare the following compounds:
(a) 4-({3-[7-(3,3-dimethyl-2-oxobutyl)-9-oxa-3,7-diazabicyclo[3.3.1]non-3-yl]propyl}amino)benzonitrile:

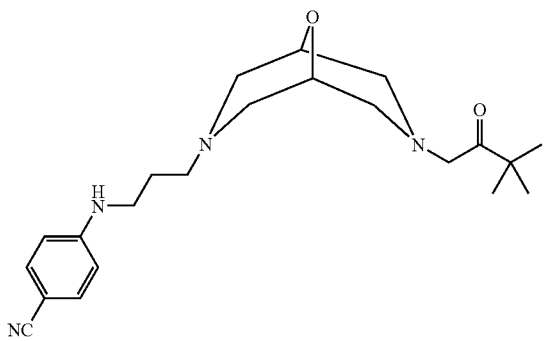

(b) tert-butyl 2-{7-[3-(4cyanoanilino)propyl]-9-oxa-3,7-diazabicyclo-[3.3.1]non-3-yl}ethylcarbamate:

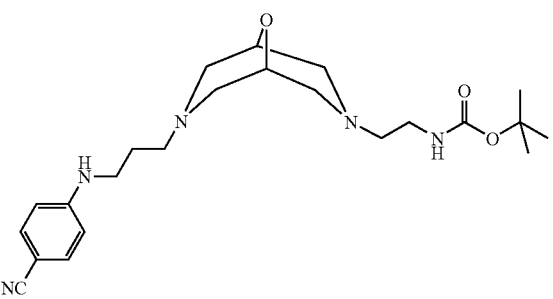

(c) tert-butyl 2-{7-[4(4-(cyanophenyl)butyl]9-oxa-3,7-diazabicyclo-[3.3.1]non-3-yl}ethylcarbamate:

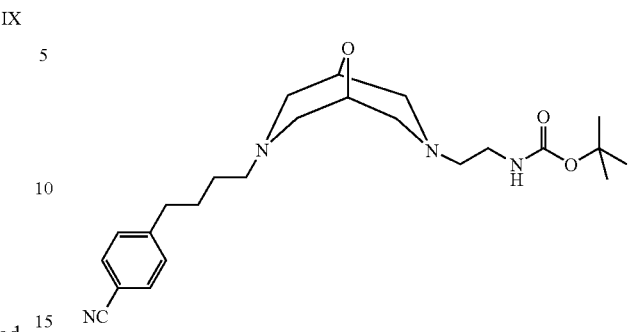

(d) tert-butyl 2-{7-[(2S)-3-(4-cyanophenoxy)-2-hydroxypropyl]-9-oxa-3,7-diazabicyclo[3.3.1]non-3-yl}ethylcarbamate:

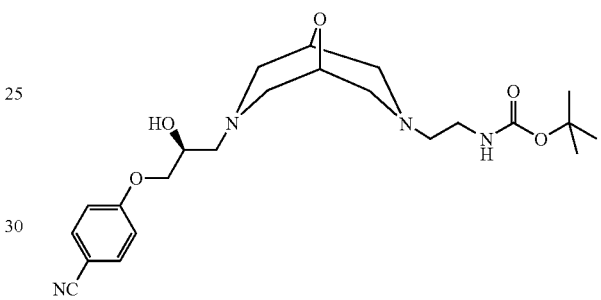

Compounds (a) to (d) may be prepared, for example, from compounds of formula I in which:
$R^1$ represents —$S(O)_2R^9$, wherein $R^9$ represents optionally substituted phenyl, such as 2- or 4-fluorophenyl, 2- or 4-chlorophenyl, 4-bromophenyl, 4-methylphenyl, 4-methoxyphenyl, 2-nitrophenyl, 2,4-dinitrophenyl, 2,4,6-trimethylphenyl and, especially, unsubstituted phenyl or 4-nitrophenyl;
$R^{41}$ to $R^{46}$ all represent H;
G represents CH;
A and B both represent direct bonds;
$R^2$ and $R^3$ independently represent H or $C_{1-6}$ alkyl; and
$R^4$ is absent or represents one to three halo, methyl, methoxy or nitro groups, such as 2- or 4-fluoro, 2- or 4-chloro, 4-bromo, 4-methyl, 2,4,6-trimethyl, 4-methoxy, or 2- or 4-nitro,
for example as described in international patent application WO 01/28992, the relevant disclosures in which document are hereby incorporated by reference.

Compounds of formula III in which the substituent $R^{42}$ has the same identity as $R^{41}$, $R^{44}$ has the same identity as $R^{43}$ and $R^{46}$ has the same identity as $R^{45}$ may be prepared by reaction of two or more equivalents of a compound of formula X,

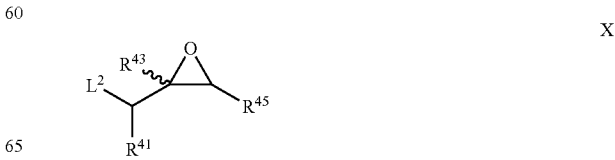

X wherein the wavy bond indicates optional R—, S— or mixed R— and S— stereochemistry at the asymmetric carbon atom, and $L^2$, $R^{41}$, $R^{43}$ and $R^{45}$ are as hereinbefore defined, with one equivalent of a compound of formula XI, $$R^1NH^2 \qquad \qquad XI$$

wherein $R^1$ is as hereinbefore defined, for example at between room and reflux temperature in the presence of a suitable base (e.g. an alkali metal carbonate such as cesium carbonate, sodium hydroxide, sodium hydride or lithium diisopropylamide), an appropriate solvent (e.g. acetonitrile, N,N-dimethylformamide, TBF, toluene, water or mixtures thereof), and optionally in the presence of a phase transfer catalyst (e.g. tricaprylyl-methylammonium chloride). Preferred bases include sodium hydroxide and preferred solvents include water. The reaction is advantageously performed with compounds of formula XI wherein $R^1$ represents —C(O)XR$^7$, —C(O)N(R$^8$)R$^{5d}$ or —S(O)$_2$R$^9$ and R$^{5d}$, R$^7$, R$^8$ and R$^9$ are as hereinbefore defined. The reaction is more advantageously performed with compounds of formula XI wherein $R^1$ represents —S(O)$_2$R$^9$ (e.g. wherein R$^9$ represents optionally substituted phenyl, such as 2- or 4-fluorophenyl, 2- or 4-chlorophenyl, 4-bromophenyl, 4-methylphenyl, 4-methoxyphenyl, 2- or 4-nitrophenyl, 2,4,6-trimethylphenyl). The use of such ring-substituted benzenesulfonyl derivatives may have the advantage that purification of the resulting compound of formula III may be made more straightforward (e.g. requiring only a simple recrystallisation step).

Compounds of formula III may alternatively be prepared by oxidation of a corresponding compound of formula XII,

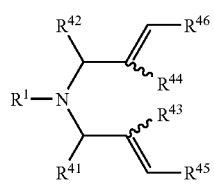

wherein the wavy bonds indicate optional E-, Z- or mixed E- and Z- geometry about the double bonds, and $R^1$ and $R^{41}$ to $R^{46}$ are as hereinbefore defined. Suitable conditions for this oxidation include, for example, reaction at between −25° C. and reflux temperature with a suitable peroxide or peracid (e.g. hydrogen peroxide, tert-butyl hydroperoxide or mCPBA), optionally in the presence of an appropriate solvent (e.g. dichloromethane, t-butanol, nitromethane, toluene, water, acetonitrile, or mixtures thereof), a suitable catalyst (for example a protic acid, a Lewis acid, or a metal complex capable of forming a peroxide adduct, such as methyltrioxorhenium(VII) or a combination of sodium tungstate and (aminomethyl)phosphonic acid), or a pre-mixed catalyst system (such as 1,4,7-trimethyl-1,4,7-triazacyclononane, along with manganese (II) acetate tetrahydate), and/or further appropriate additives (for example: in the case of oxidations carried out with methyltrioxorhenium(VII) and hydrogen peroxide, a basic additive such as pyridine or pyrazole; and in the case of oxidations with sodium tungstate and hydrogen peroxide, a phase transfer catalyst such as methyltri-n-octylammonium hydrogensulfate). (See for example European patent application EP 0 380 085 and international patent application WO 98/33786, the disclosures in which documents are hereby incorporated by reference.)

Compounds of formula XII in which $R^1$ represents —C(O)XR$^7$, —C(O)N(R$^8$)R$^{5d}$ or —S(O)$_2$R$^9$ may be prepared by reaction of a compound of formula XII,

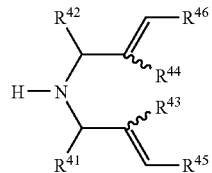

wherein the wavy bonds indicate optional E-, Z- or mixed E- and Z-geometry about the double bonds, and $R^{41}$ to $R^{46}$ are as hereinbefore defined with a compound of formula XI, $$R^{1b}\text{-}L^1 \qquad \qquad XIV$$

in which $R^{1b}$ represents —C(O)XR$^7$, —C(O)N(R$^8$)R$^{5d}$ or —S(O)$^2$R$^9$ and L$^1$, R$^{5d}$, R$^7$, R$^8$ and R$^9$ are as hereinbefore defined (L$^1$ is preferably halo, such as chloro), for example at between −10 and 25° C. optionally in the presence of a suitable base (e.g. NaOH, triethylamine, pyridine or potassium carbonate) and an appropriate solvent (e.g. ether, water, dichloromethane, THF, tert-butyl methyl ether, or mixtures thereof).

Compounds of formulae IV, VI, VIII, IX, X, M, XIII and XIV and derivatives thereof, are either commercially available, are known in the literature, or may be obtained either by analogy with the processes described herein or in the literature (see, for example, international patent application WO 01/28992), or by conventional synthetic procedures, in accordance with standard techniques from readily available starting materials using appropriate reagents and reaction conditions. For example, compounds of formulae IV, VIII and IX may be prepared analogously to processes described in international patent application WO 01/28992, the relevant disclosures in which document are hereby incorporated by reference. Further, compounds of formula XI in which $R^1$ represents —SO$_2$R$^9$, and R$^9$ represents 4-nitrophenyl may be prepared by reaction of ammonia with 4-nitrobenzenesulfonyl chloride, for example as described hereinafter.

Compounds of formula I, and intermediates described herein, may be isolated from their reaction mixtures using conventional techniques.

It will be appreciated by those skilled in the art that, in the processes described above, the functional groups of intermediate compounds may be, or may need to be, protected by protecting groups.

Functional groups which it is desirable to protect include hydroxy, amino and carboxylic acid. Suitable protecting groups for hydroxy include trialylsilyl and diarylalkylsilyl groups (e.g. tert-butyldimethylsilyl, tert-butyldiphenylsilyl or trimethylsilyl), tetrahydropyranyl and alkylcarbonyl groups (e.g. methyl- and ethylcarbonyl groups). Suitable protecting groups for amino include benzyl, sulfonamido (e.g. benzenesulfonamido), tert-butyloxycarbonyl, 9-fluorenyl-methoxycarbonyl or benzyloxycarbonyl. Suitable protecting groups for amidino and guanidino include benzyloxycarbonyl. Suitable protecting groups for carboxylic acid include $C_{1-6}$ alkyl or benzyl esters.

The protection and deprotection of functional groups may take place before or after any of the reaction steps described hereinbefore.

Protecting groups may be removed in accordance with techniques which are well known to those skilled in the art and as described hereinafter. For example, we have found that removal of an —SO$_2$R$^9$ group from an oxabispidine ring may take place conveniently by employment of an appropriate strong acid, such as a hydrohalic acid (especially HBr) e.g. as described herein.

The use of protecting groups is fully described in "Protective Groups in Organic Chemistry", edited by J. W. F. McOmie, Plenum Press (1973), and "Protective Groups in Organic Synthesis", 3$^{rd}$ edition, T. W. Greene & P. G. M. Wutz, Wiley-Interscience (1999).

Persons skilled in the art will appreciate that, in order to obtain compounds of formula I (and intermediates described herein) in an alternative, and, on some occasions, more convenient, manner, the individual process steps mentioned herein may be performed in a different order, and/or the individual reactions may be performed at a different stage in the overall route (i.e. substituents may be added to and/or chemical transformations performed upon, different intermediates to those associated hereinbefore with a particular reaction). This will depend inter alia on factors such as the nature of other functional groups present in a particular substrate, the availability of key intermediates and the protecting group strategy (if any) to be adopted. Clearly, the p of chemistry involved will influence the choice of reagent that is used in the said synthetic steps, the need, and type, of protecting groups that are employed, and the sequence for accomplishing the synthesis.

The process of the invention may have the advantage that oxabispidine ring systems may be formed using fewer steps than methods described in the prior art Further, the process for making compounds of formula I from compounds of formulae III and IV (i.e. via compounds of formula II), in particular avoids the use of mercury-containing compounds (thereby eliminating the production of toxic, mercury-containing waste). This process offers a convenient synthetic route to key oxabispidine compounds, and allows differential protection at the nitrogen atoms.

Further, this process may have the advantage that it is scalable, and that compounds comprising the oxabispidine ring may be prepared in less time, more conveniently, and/or at a lower cost, than when prepared in processes described in the prior art.

According to a further aspect of the invention there is provided a compound of formula II, as hereinbefore defined, or a protected derivative thereof The invention is illustrated by way of the following examples.

EXAMPLES

General Experimental Procedures

Mass spectra were recorded on one of the following instruments: a Waters ZMD single quad with electrospray (SIN mc350); a Perkin-Elmer SciX API 150ex spectrometer; a VG Quattro II triple quadrupole; a VG Platform II single quadrupole; or a Micromass Platform LCZ single quadrupole mass spectrometer (the latter three instruments were equipped with a pneumatically assisted electrospray interface (LC-MS)). $^1$H NMR and $^{13}$C NMR measurements were performed on Varian 300, 400 and 500 spectrometers, operating at $^1$H frequencies of 300, 400 and 500 MHz respectively, and at $^{13}$C frequencies of 75.5, 100.6 and 125.7 MHz respectively. Alternatively, $^{13}$C No measurements were performed on a BRUKER ACE 200 spectrometer at a frequency of 50.3 MHz.

Rotamers may or may not be denoted in spectra depending upon ease of interpretation of spectra. Unless otherwise stated, chemical shifts are given in ppm with the solvent as internal standard.

Examples 1 to 3

Preparation of Oxabispidine Ring System

Example 1

3-Benzyl-7-(phenylsulfonyl)-9-oxa-3,7-diazabicyclo [3.3.1]nonane (i) N,N-Bis(2-oxiranylmethyl)benzenesulfonamide Water (2.5 L, 10 vol.) followed by epichlorohydrin (500 mL, 4 eq.) were added to benzenesulfonamide (250 g, 1 eq.). The reactants were heated to 40° C. Aqueous sodium hydroxide (130 g in 275 mL of water) was added such that the temperature of the reaction remained between 40° C. and 43° C. This took approximately 2 hours. (The rate of sodium hydroxide addition needs to be slower at the start of the addition than at the end in order to keep within the temperature range stated.) After the addition of sodium hydroxide was complete, the reaction was stirred at 40° C. for 2 hours, then at ambient temperature overnight. The excess epichlorohydrin was removed as a water azeotrope by vacuum distillation (ca. 40 mbar, internal temp 30° C.), until no more epichlorohydrin distilled. Dichloromethane (1 L) was added and the mixture stirred rapidly for 15 minutes. The phases were allowed to separate (this took 10 minutes although totally clear phases are obtained after standing overnight). The phases were separated and the dichloromethane solution used in the subsequent step below.

$^1$H NMR (400 MHz, CDCl$_3$): δ 2.55-2.65 (2H, m), 2.79 (2H, t, J 4.4), 3.10-3.22 (4H, m), 3.58-3.73 (2H, m), 7.50-7.56 (2H, m), 7.58-7.63 (1H, m), 7.83-7.87 (2H, m).

(ii) 5-Benzyl-3,7-dihydroxy-1-phenylsulfonyl-1,5-diazacyclooctane

IMS (2.5 L, 10 vol) was added to the dichloromethane solution from step (i) above. The solution was distilled until the internal temperature reached 70° C. Approximately 1250 mL of solvent was collected. More IMS (2.5 L, 10 vol) was added followed by benzylamine (120 mL, 0.7 eq.) in one portion (no exotherm seen), and the reaction was heated at reflux for 6 hours (no change from 2 hour sampling point). More benzylamine was added (15 mL) and the solution was heated for a further 2 hours. The IMS was distilled off (ca. 3.25 L) and toluene was added (2.5 L). More solvent was distilled (ca. 2.4 L) and then further toluene added (1 L). The head temperature was now 110° C. A further 250 mL of solvent was collected at 110° C. Theoretically, this left the product in ca. 2.4 L of toluene at 110° C. This solution was used in the next step.

$^1$H NMR (400 MHz, CDCl$_3$): δ 7.83-7.80 (4H, m, ArH), 7.63-7.51 (6H, m, ArH), 7.30-7.21 (10H, m, ArH), 3.89-3.80 (4H, m, CH(a)+CH(b)), 3.73 (2H, s, CH$_2$Ph(a)), 3.70 (2H, s, CH$_2$Ph(b)), 3.59 (2H, dd, CHHNSO$_2$Ar(a)), 3.54 (2H, dd, CHHNSO$_2$Ar(b)), 3.40 (2H, dd, CHHSO$_2$Ar(b)), 3.23 (2H, dd, CHHNSO$_2$Ar(a)), 3.09-2.97 (4H, m, CHHNBIn(a)+Cn (b)), 2.83 (2H, dd, CHHNBn(b)), 2.71 (2H, dd, CHNBn(a))

(Data taken from purified material comprising a 1:1 mixture of trans- (a), and cis-diol (b))

(iii) 3-Benzyl-7-(phenylsulfonyl)-9-oxa-3,7-diazabicyclo[3.3.1]nonane

The toluene solution from the previous step (ii) above was cooled to 50° C. Anhydrous methanesulfonic acid (0.2 L) was added. This caused a temperature rise from 50° C. to 64° C. After 10 minutes, methanesulfonic acid was added (1 L) and the reaction heated to 110° C. for 5 hours. Toluene was then distilled from the reaction; 1.23 L was collected. (Note that the internal temperature should not be allowed higher than 110° C. at any stage otherwise the yield will be decreased.) The reaction was then cooled to 50° C. and a vacuum applied to remove the rest of the toluene. Heating to 110° C. and 650 mbar allowed a further 0.53 L to be removed. (If the toluene can be removed at a lower temperature and pressure then that is is beneficial.) The reaction was then left to cool to 30° C. and deionised water (250 mL) was added. This caused the temperature to rise from 30° C. to 45° C. More water (2.15 L) was added over a total time of 30 minutes such that the temperature was less than 54° C. The solution was cooled to 30° C. and then dichloromethane (2 L) was added. With external cooling and rapid stirring, the reaction mixture was basified by adding aqueous sodium hydroxide (10 M, 2 L) at a rate that kept the internal temperature below 38° C. This took 80 minutes. The stilling was stopped and the phases separated in 3 minutes. The layers were partitioned. IMS (2 L) was added to the dichloromethane solution and distillation started. Solvent (2.44 L) was collected until the head temperature reached 70° C. Theoretically, this left the product in 1.56 L of IMS. The solution was then allowed to cool to ambient temperature overnight with slow stirring. The solid product that precipitated was filtered and washed with IMS (0.5 L) to give a fawn-coloured product that, on drying at 50° C., in vacuum, gave 50.8 g (8.9% over 3 steps). –20.0 g of this product was dissolved in acetonitrile (100 mL) at reflux to give a pale yellow solution. After cooling to ambient temperature, the crystals that formed were collected by filtration and washed with acetonitrile (100 mL). The product was dried in vacuo at 40° C. for 1 hour to give 17.5 g (87%) of sub-title compound.

$^1$H NMR (400 MHz, CDCl3): δ 7.18-7.23 (10H, m), 3.86-3.84 (2H, m), 3.67 (2H, d), 3.46 (2H, s), 2.91 (2H, d), 2.85 (2H, dd), 2.56 (2H, dd).

Example 2

3-Benzyl-7-(4-nitrophenylsulfonyl)-9-oxa-3,7-diazabicyclo[3.3.1]-nonane

(i) N,N-Bis-(2-oxiranylmethyl)-4-nitrobenezenesulfonamide

Alternative I

(a) 4-Nitrobenzenesulfonamide

A solution of 4-nitrobenzenesulfonyl chloride (1.242 kg) in dichloromethane (3.7 L) was filtered to remove insoluble material (ca. 5 g) and then added portion wise over 2 hours to concentrated aqueous ammonia (2 L) such that the temperature was 5° C. (±5° C.). After the addition was complete, the product was collected by filtration and washed with water (3.5 L). The solid was sucked dry on the filter for 1 hour. The damp product was dissolved in methanol:water (4:1, 6.190 L) at reflux. The solution was allowed to cool naturally from reflux to ambient temperature. The solid precipitate was collected by filtration, washed with methanol:water (4:1, 1.5 L), then sucked dry on the filter. Final drying at 40° C. in vacuo gave 0.812 kg (72%) of the sub-title product.

(b) N,N-Bis-(2-oxiranylmethyl)$^4$-nitrobenezenesulfonamide

Water (2.25 L), then epichlorohydrin (387 mL), where added to 4-nitrobenzenesulfonamide (250 g, see step (a) above). The reactants were heated to 40° C. Aqueous sodium hydroxide (100.9 g in 250 mL of water) was added such that the temperature of the reaction remained between 40° C. and 43° C. (This takes at least two hours. The rate of sodium hydroxide addition may need to be slower at the start of the addition than at the end in order to keep within the temperature range stated) After the addition of sodium hydroxide was complete, the reaction was stirred at 40° C. overnight (approximately 16 hours). The excess epichlorohydrin was removed as a water azeotrope by vacuum distillation (ca. 80 mbar, internal temp 40° C.) until no more epichlorohydrin distilled. The pH was checked and found to be neutral. Ethyl acetate (3.75 L) was added and the mixture stirred rapidly for at least 15 minutes at 40° C. The phases were allowed to separate (this took 5 minutes). The aqueous phase was re-extracted with ethyl acetate (1.25 L). The combined organic extracts were filtered through kieselguhr. (An aqueous phase often appears at this stage and, if so, the layers are separated again.) The organic solution was then concentrated in vacuo at 30° C. The resulting crude solid (which is sometimes an oil) was slurried in methanol (875 mL, 3.5 vol.), heated to reflux (does not dissolve) and then allowed to cool slowly to room temperature with rapid stirring. After further cooling to 0° C., the product was collected by filtration and washed with cold methanol (250 mL) to give a yellow solid. Driving at 40° C. in vacuo gave 241.5 g (62%) of the sub-title compound.

Alternative 2

(a) N,N-Diallyl 4-nitrobenzenesulfonamide

Alternative I

Diallylamine (68.5 mL) was added dropwise with cooling to a rapidly stirred solution of 4-nitrobenzenesulfonyl chloride (115.91 g) in dichloromethane (1.16 L) at 5° C. After 2 hours stirring, aqueous sodium hydroxide (10 M, 65.4 mL) was added dropwise with cooling. The layers were separated and the organic phase was washed with aqueous hydrochloric acid (2M, 465 mL). The organic phase was concentrated in vacuo to give the product as a solid (140.19 g, 95%). (The product can be recrystallised if necessary.)

m.p. 64-65° C. (from TMBE)

$^1$H NMR (300 MHz; CDCl$_3$): δ 8.38-8.34 (2H, m), 8.04-7.99 (2H, m), 5.67-5.56 (2H, m), 5.22-5.14 (4H, m) and 3.88 (4H, d)

Alternative II

Diallylamine (120 mL) was added dropwise with cooling to a rapidly stirred solution of 4-nitrobenzenesulfonyl chloride (202.0 g) in tert-butyl methyl ether (2 L) at 5° C. The reaction was completed, after an overnight stir out for convenience. Aqueous sodium hydroxide (10M, 114 mL) was added dropwise with cooling. Water (1.4 L) was added and the layers were then separated. The organic phase was washed with aqueous hydrochloric acid (2M, 0.8 L). The organic layer was then washed with water (2×0.8 L and 1×0.4 L) until the aqueous layer remained neutral as measured by pH paper. The organic layer was diluted with IMS (1.5 L) and then solvent was removed by distillation (2.5 L). On cooling, the product precipitated (efficient stirring is necessary). The solid was then collected by filtration and was washed with cold IMS (0.5 L) to give 192.51 g (75%).

(b) N,N-Bis-(2-oxiranylmethyl)-4-nitrobenezenesulfonamide

Alternative I

Methyltrioxorhenium(VII) (MTO) (88 mg, 0.35 mol), pyrazole (578 mg, 8.4 mmol) and hydrogen peroxide (30%, 16 mL, 140 mmol) were added to a stirred solution of N,N-diallyl 4-nitrobenzenesulfonamide (10 g, 35 mmol, see step (a) above) in dichloromethane (20 mL). Over 48 hours, a further four additions of MTO (4×88 mg, 4×0.35 mmol) were made, at regular intervals. The solution was stirred for a further 24 hours. Dichloromethane (200 mL) and water (200 mL) were added to the reaction mixture. The dichloromethane layer was separated and washed with aqueous hydrochloric acid (2M, 100 mL), brine (100 mL), and then aqueous sodium sulfite solution (10% w/v, 100 ml). The organic phase was then concentrated under reduced pressure to give the product as an off-white solid (10.65 g, 97%).

m.p. 101.1-102° C.

$^1$H NMR (300 MHz, CDCl$_3$): δ 8.39 (2H, dd), 8.08 (2H, dd), 3.88-3.73 (2H, m), 3.27-3.12 (4H, m), 2.82 (2H, td) and 2.63-2.58 (2H, m) $^{13}$C NMR (400 MHz, CDCl$_3$): δ 150.1, 145.4, 128.5, 128.4, 124.5, 124.4, 51.6, 51.0, 50.4, 50.0 and 45.2

Alternative II

A pre-mixed catalyst system: TMTACN (1,4,7-trimethyl-1,4,7-triazacyclononane, prepared as an approximately 60 mM solution in acetonitrile 58.4 mM, 27.3 mL, 0.006 mol eq.), manganese (II) acetate tetrahydate (150 mM, 8.0 mL, 0.0045 mol eq., prepared as a 150 mM solution in water) and equimolar ascorbic acid and sodium ascorbate (80 mM, 12.0 mL, 0.0036 mol eq., prepared as a 80 mM (of both) solution in water) was added to acetonitrile (375 mL, 5 vol) at 10° C. The combined mixture was allowed to equilibrate at 10° C. An initial charge of hydrogen peroxide (35% w/w, 15.5 g, 0.6 mol eq) was added over ten minutes. With this addition, a colour change from colourless to dark brown was noticed accompanied by an exotherm and effervescing. (For this reason it is best to carry out this experiment in a temperature controlled reaction vessel with appropriate off-gassing capability.) The combined mixture was re-cooled to 10° C. A solution of pre-prepared N,N-diallyl 4-nitrobenzenesulfonamide (75.0 g, 1.0 mol eq., see step (a) above) in acetonitrile (375 mL, 5 vol.) was added. The combined mixture was allowed to equilibrate at 10° C. Further hydrogen peroxide (35% w/w, 139.4 g, 5.4 mol eq) was added over one hour, whilst maintaining the temperature at 10° C. (The reaction requires an additional stir out at 10° C., this can be up to 16 hours.) Once completed the reaction was quenched by the addition of 10% w/w sodium sulfite (300 mL, 4 vol) over about fifteen minutes, whilst maintaining the temperature at 10° C. (the sodium sulfite was added with portion-wise monitoring for peroxide by way of a test stick). tert-Butyl methyl ether (TBME) (1.5 L, 20 vol) was added, and the resulting layers were separated. The organic layer was swapped into LMS, and the amount of solvent was reduced to about 1.05 L (14 vol.). The product precipitated on cooling to less than 10° C., and was isolated by filtration. The crude solid was washed with IMS (300 mL, 4 vol) and was then dried in a vacuum oven at 40° C. overnight to give the title compound as a white solid, 60.75 g, 73%.

m.p. 98.4-100.6° C.

$^1$H NMR (CDCl$_3$, 400 MHz): δ 8.36-8.39 (2H), 8.05-8.08 (2H), 3.73-3.85 (2H), 3.14-3.25 (2H), 2.80-2.83 (2H), 2.58-2.60 (2H)

(ii) 3-Benzyl-7-(4-nitrophenylsulfonyl)-9-oxa-3,7-diazabicyclo[3.3.1]-nonane (Prepared by Way of In Situ Formation of Diol)

Alternative 1

Benzylamine (1.39 mL) was added under nitrogen at room temperature to a mixture of N,N-bis-(2-oxiranylmethyl)-4-nitrobenezenesulfonamide (5.0 g, see step (i) above), ethanol (90 mL) and ethyl acetate (10 mL). The mixture was then heated at reflux for 2 h after which time more benzylamine was added (0.7 mL) and heating continued overnight. The mixture was distilled and solvent was collected (50 mL). Chlorobenzene (100 mL) was added and distillation was continued until a further 50 mL of solvent was collected. The solution was allowed to cool to 22° C. and was then treated with water (1.34 mL) and then conc. sulfuric acid (13.4 mL) The internal temperature rose to 30° C. The mixture was then heated to 75° C. for 3 hours before being allowed to cool to room temperature. Ethanol (26 mL) was added in one portion (temp rise to 30° C.). The mixture was then neutralised by the addition of ammonia (17.5% aqueous solution, 60 mL) over 15 min with rapid stirring but no external cooling. The internal temperature rose to 78° C. The biphasic mixture was transferred to a separating funnel (whilst hot) and the chlorobenzene layer was separated, cooled to room temperature and reduced in volume by approximately half by rotary evaporation. Methanol (50 mL) was added which caused the precipitation of a yellow solid, which was filtered and washed with methanol (20 mL). The solid was then dried to constant weight (1.931 g, 30% yield) on a rotary evaporator at 50° C.

(The above reaction can also be performed using 1 vol. of sulfuric acid, which reduces the amount of ammonia required in the work up by half. The chlorobenzene volume can also be reduced to 7 volumes.)

Alternative 2

N,N-Bis-(2-Oxiranylmethyl)-4-nitrobenezenesulfonamide (20.0 g, see step (i) above) in IMS (400 mL) was treated with benzylamine (6.95 mL) and the mixture was heated at reflux for 16 hours. The solvent was swapped for toluene by atmospheric pressure distillation to leave the crude product in 150 mL of toluene. Methanesulfonic acid (50 mL) was added to the toluene solution at 32° C. over 10 min. (caution-exothermic, internal temp. rises to 50° C.). The mixture was heated to 110° C. Toluene (50 mL) was removed by distillation. Heating was continued at 110° C. for 14 hours. The mixture was allowed to cool to 40° C. and then the remaining toluene was removed by reduced pressure distillation (40 mbar). Water (150 mL) was added over 20 minutes, whilst maintaining the internal temperature below 50° C. Dichloromethane (150 mL) was added at 32° C. and the mixture then cooled to 20° C. Sodium hydroxide (125 mL) was added at a rate such that the internal temperature remained below 35° C. The resulting biphasic mixture was cooled to 20° C. (some material came out of solution so a further 50 mL of dichloromethane was added) and the organic layer was separated. A solvent swap for IMS by atmospheric pressure distillation to leave a total of 100 mL of IMS caused precipitation of the product as a pale brown solid, which was filtered and washed with a further 50 mL of IMS. The product was dried at 50° C. on a rotary evaporator to give 7.56 g of the title compound (32%).

Example 3

3-Benzyl-7-(phenylsulfonyl)-9-oxa-3,7-diazabicyclo [3.3.1]nonane (i) N,N-Bis(2-oxiranylmethyl)benzenesulfonamide Water (500 mL, 10 vol) followed by epichlorohydrin (100 ml, 4 equiv.) were added to benzenesulfonamide (50 g, 1 equiv.). The reactants were heated to 40° C. Aqueous sodium hydroxide (65 mL of 40% aqueous solution, 2.04 equiv.) was added at a rate such that the temperature of the reaction remained between 40° C. and 43° C. After the addition of sodium hydroxide was complete (90 min.), the reaction mixture was stirred at 40° C. for 2 hours and then at ambient temperature overnight. Excess epichlorohydrin was removed as a water azeotrope by vacuum distillation (ca. 60 mbar, internal temp. 40° C.) until no more epichlorohydrin distilled (approx. 50 mL of distillate was collected). Chlorobenzene (100 mL, 2 vol.) was added and the mixture was stirred rapidly for 15 minutes. Stirring was stopped and two phases formed within 30 seconds. The phases were separated and the chlorobenzene solution was used directly in the next step.

(ii) 5-Benzyl-3,7-dihydroxy-1-phenylsulfonyl-1,5-diazacyclooctane

Ethanol (900 mL, 18 vol) was added to the chlorobenzene solution from step (i) above. Benzylamine (24.3 mL, 0.7 equiv.) was added in one portion (no exotherm seen) and the reaction was heated at reflux for 3 hours. More benzylamine was added (4.8 mL) and the solution was heated for a further 3 hours. More benzylamine (2.4 mL) was added and the mixture was heated at reflux for 1 hour. Ethanol (500 mL) was removed by atmospheric pressure distillation. Chlorobenzene (200 mL) was added and a further 400 mL of solvent was removed by distillation. Chlorobenzene (100 mL) was added and 150 mL of solvent was removed by reduced pressure distillation (50 mbar). The crude product (now theoretically in 250 mL of chlorobenzene) was used in the next step.

(iii) 3-Benzyl-7-(phenylsulfonyl)-9-oxa-3,7-diazabicyclo[3.3.1]nonane

The chlorobenzene solution from step (ii) above was treated at 50° C. with water (6 mL) and then concentrated sulfuric acid (60 mL) was added over 10 min. whilst maintaining the temperature at between 50 and 60° C. The mixture was then heated to 110° C. for 1 hour. The mixture was allowed to cool to 50° C. and EtOH (60 mL) was added in one portion, causing the internal temperature to rise to 67° C. The mixture was basified by the addition of aqueous ammonia (17.5%, 300 mL) with external cooling to keep the internal temperature between 60 and 70° C. Chlorobenzene (600 mL) was added and the mixture was stirred rapidly for 10 minutes. The mixture was allowed to settle and the layers were separated. The upper (chlorobenzene) layer was subjected to reduced pressure (50 mbar) distillation to remove 380 mL of solvent. The mixture was allowed to cool to 50° C. and 480 mL of ethanol was added. The mixture was cooled to 7° C. and the resulting solid was filtered and washed with ethanol (2×50 mL) before drying to constant weight under reduced pressure at 40° C. The product was obtained as an off white solid, 10.25 g (9.0% yield).

Examples 4 and 5

Deprotection of 7-Phenylsulfonyl-Derivatives of 3-Benzyl-9-oxa-3,7-diazabicyclo[3.3.1]nonanes to give 3-Benzyl-9-oxa-3,7-diazabicyclo-[3.3.1]nonane Example 4

Concentrated hydrobromic acid (1.2 L, 3 rel. vol.) was added to solid 3-benzyl-7-(phenylsulfonyl)-9-oxa-3,7-diazabicyclo[3.3.1]nonane (400 g, see Example 1 above) and the mixture was heated to reflux under a nitrogen atmosphere. The solid dissolved in the acid at 95° C. After heating the reaction for 8 hours, HPLC analysis showed that the reaction was complete. The contents were cooled to room temperature. Toluene (1.2 L, 3 rel. vol.) was added and the mixture stirred vigorously for 15 minutes. Stirring was stopped and the phases were partitioned. The toluene phase was discarded along with a small amount of interfacial material. The acidic phase was returned to the original reaction vessel and sodium hydroxide (10 M, 1.4 L, 3.5 rel. vol.) was added in one portion. The internal temperature rose from 30° C. to 80° C. The pH was checked to ensure it was >14. Toluene (1.6 L, 4 rel. vol.) was added and the temperature fell from 80° C. to 60° C. After vigorous stirring for 30 minutes, the phases were partitioned. The aqueous layer was discarded along with a small amount of interfacial material. The toluene phase was returned to the original reaction vessel, and 2-propanol (4 L, 10 rel. vol.) was added. The temperature was adjusted to between 40° C. and 45° C. Concentrated hydrochloric acid (200 mL) was added over 45 minutes such that the temperature remained at between 40° C. and 45° C. A white precipitate formed. The mixture was stirred for 30 minutes and then cooled to 7° C. The product was collected by filtration, washed with 2-propanol (0.8 L, 2 rel vol.), dried by suction and then further dried in a vacuum oven at 40° C.

Yield=297 g (91%).

$^1$H NMR (CD$_3$OD+4 drops D$_2$O): δ 2.70 (br d, 2H), 3.09 (d, 2H), 3.47 (br s, 4H), 3.60 (s, 2H), 4.12 (brs, 2H), 7.30-7.45 (mn, 5H).

API MS: m/z=219 [C$_{13}$H$_{18}$N$_2$O+H]$^+$.

Example 5

(a) Pre-Formation and Isolation of Mercaptoacetic Acid Di-lithium Salt Monohydrate Finely crushed lithium hydroxide (1.03 g, 43 mmol) was added to a solution of mercaptoacetic acid (1.5 mL, 1.97 g, 21.5 mmol) in 2-propanol (20 mL). The mixture was stirred for 1.5 hours at room temperature. All solvent was removed by rotary evaporation. This gave a fine white powder (2.55 g, 97%). The mass recovery and NMR suggest that the salt forms as a monohydrate.

(b) 3-Benzyl-9-oxa-3,7-diazabicyclo[3.3.1]nonane×2HCl

1-Methyl-2-pyrrolidinone (10 mL) was added to mercaptoacetic acid di-lithium salt monohydrate (from part (a) above, 1.21 g, 10 mmol) and the mixture was stirred for 10 minutes at room temperature. 3-Benzyl-7-(4-nitrophenylsulfonyl)-9-oxa-3,7-diazabicyclo[3.3.1]nonane (2 g, 5 mmol, see Example 2 above) was added and the mixture stirred at room temperature under nitrogen for 2.5 hours. Toluene (8 mL) and 2-propanol (15 mL) were added to the bright orange reaction solution. The internal temperature was adjusted to 40-45° C. A solution of hydrogen chloride in 2-propanol (10 mL, approx. 4M) was added dropwise whilst maintaining the above internal temperature range. Stirring was continued for 30 minutes in this temperature range. A white precipitate formed and the mixture was cooled slowly to room temperature with stirring. The mixture was stirred overnight and then cooled in an ice/water bath to 7° C. The precipitate was collected by filtration, washed with 2-propanol (2×5 mL) and sucked dry on the filter to give the title compound as a white powder (1.28 g, 88%).

$^1$H NMR (300 MHz, D$_2$O): δ 7.50 (5H, s), 4.06 (2H, br s), 3.91 (2H, br s), 3.50-3.61 (4H, m), 3.39 (2H, d) and 3.08 (2H, br s)

(If necessary, 3-benzyl-9-oxa-3,7-diazabicyclo[3.3.1] nonane×2HCl can be recrystallised from methanol: 2-propanol (5 vol: 2 vol) with a recovery of approximately 80%. It is important to note when carrying out the recrystallisation that the 2-propanol should only be added once all the salt has dissolved in the methanol (this occurs as the methanol approaches reflux).)

The invention claimed is:

1. A compound of formula II

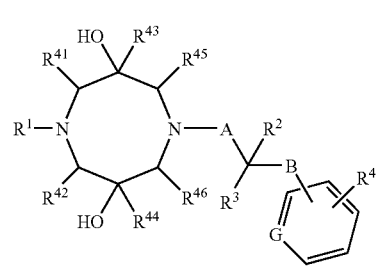

II wherein
A represents C$_1$ alkylene or linear C$_2$ alkylene;
B represents -Z-, -Z-N(H)— or -Z-O— in which latter two groups, Z is attached to the carbon atom bearing R$^2$ and R$^3$ and represents C$_1$ alkylene or linear C$_2$ alkylene;
Z represents a direct bond or C$_{1-4}$ alkylene;
G represents CH;
R$^1$ represents straight— or branched-chain C$_{1-4}$ alkyl terminated by C(O)R$^{5a}$ or —N(H)C(O)OR$^{10b}$.
R$^{5a}$ and R$^{10b}$ independently represent straight— or branched-chain C$_{2-6}$ alkyl;
R$^2$ represents H or OH;
R$^3$ represents H;
R$^4$ is a single cyano group in the para-position relative to B;
R$^{41}$ to R$^{46}$ all represent H,
or a protected derivative thereof.

2. The compound 5-benzyl-3,7-dihydroxy-1-phenylsulfonyl -1,5-diazacyclooctane.

* * * * *